United States Patent
Northcutt et al.

(10) Patent No.: US 11,331,199 B2
(45) Date of Patent: May 17, 2022

(54) SPINAL IMPLANT FOR MOTION PRESERVATION OR FUSION

(71) Applicant: Aurora Spine, Inc., Carlsbad, CA (US)

(72) Inventors: Trent James Northcutt, Oceanside, CA (US); Laszlo Garamszegi, Mission Viejo, CA (US)

(73) Assignee: Aurora Spine, Inc., Carlsbad, CA (US)

( * ) Notice: Subject to any disclaimer, the term of this patent is extended or adjusted under 35 U.S.C. 154(b) by 0 days.

(21) Appl. No.: 16/862,355

(22) Filed: Apr. 29, 2020

(65) Prior Publication Data

US 2021/0161677 A1    Jun. 3, 2021

Related U.S. Application Data

(60) Provisional application No. 62/840,230, filed on Apr. 29, 2019.

(51) Int. Cl.
| | |
|---|---|
| *A61F 2/44* | (2006.01) |
| *A61B 17/70* | (2006.01) |
| *A61F 2/30* | (2006.01) |
| *A61F 2/46* | (2006.01) |

(52) U.S. Cl.
CPC .......... *A61F 2/446* (2013.01); *A61B 17/7065* (2013.01); *A61B 17/7067* (2013.01); *A61F 2/30749* (2013.01); *A61F 2/4611* (2013.01); *A61F 2002/3055* (2013.01); *A61F 2002/30228* (2013.01); *A61F 2002/30286* (2013.01); *A61F 2002/30476* (2013.01); *A61F 2002/30494* (2013.01); *A61F 2002/30515* (2013.01); *A61F 2002/30604* (2013.01)

(58) Field of Classification Search
CPC ............ A61B 17/7062; A61B 17/7064; A61B 17/7065; A61B 17/7067; A61F 2/44; A61F 2/4405; A61F 2/46; A61F 2/4603; A61F 2/4611
See application file for complete search history.

(56) References Cited

U.S. PATENT DOCUMENTS

| | | | | |
|---|---|---|---|---|
| 5,645,599 A | * | 7/1997 | Samani | ............... A61B 17/7062 623/17.16 |
| 6,102,950 A | * | 8/2000 | Vaccaro | .................. A61F 2/447 623/17.16 |

(Continued)

*Primary Examiner* — Eric S Gibson
(74) *Attorney, Agent, or Firm* — Hybrid Law Group P.C.

(57) ABSTRACT

An interspinous posterior device (IPD) is described. The IPD has a body and bone fixation elements on either side of the body, each of said bone fixation elements having a ratchet locking mechanism for fixing the body to successive spinous processes of a mammalian vertebra. Each of the bone fixation elements is independently adjustable by ratcheting it separately and independently of the other bone fixation elements. The body of the IPD has a dynamic configuration and a non-dynamic configuration, wherein the dynamic configuration allows for both extension and flexion of the successive spinous processes and the non-dynamic configuration prohibits extension of the successive spinous processes. The IPD also includes a removable extension restriction block, wherein the extension restriction block can optionally be inserted in the body to prohibit extension or can be removed from the body to allow extension.

14 Claims, 7 Drawing Sheets

(56) References Cited

U.S. PATENT DOCUMENTS

| | | | | |
|---|---|---|---|---|
| 7,815,663 B2* | 10/2010 | Trieu | A61B 17/7031 | 606/254 |
| 8,968,365 B2* | 3/2015 | Aschmann | A61B 17/7053 | 606/248 |
| 9,364,267 B2* | 6/2016 | Northcutt | A61B 17/7019 | |
| 9,387,016 B2* | 7/2016 | Okamoto | A61B 17/7065 | |
| 9,414,932 B2* | 8/2016 | Errico | A61F 2/442 | |
| 9,603,637 B2* | 3/2017 | Northcutt | A61B 17/7068 | |
| 9,872,777 B2* | 1/2018 | Ganter | A61F 2/4455 | |
| 9,974,575 B2* | 5/2018 | Ponmudi | A61B 17/7068 | |
| 10,105,235 B2* | 10/2018 | Ledet | A61F 2/4455 | |
| 10,925,749 B2* | 2/2021 | Ledet | A61F 2/442 | |
| 2003/0040746 A1* | 2/2003 | Mitchell | A61B 17/7067 | 623/17.11 |
| 2005/0125063 A1* | 6/2005 | Matge | A61F 2/442 | 623/17.13 |
| 2007/0191953 A1* | 8/2007 | Trieu | A61F 2/442 | 623/17.15 |
| 2007/0225806 A1* | 9/2007 | Squires | A61F 2/442 | 623/17.11 |
| 2010/0087860 A1* | 4/2010 | Chin | A61B 17/1671 | 606/249 |
| 2010/0286777 A1* | 11/2010 | Errico | A61F 2/4455 | 623/17.11 |
| 2011/0022090 A1* | 1/2011 | Gordon | A61B 17/7068 | 606/249 |
| 2011/0153020 A1* | 6/2011 | Abdelgany | A61F 2/4465 | 623/17.16 |
| 2011/0319936 A1* | 12/2011 | Gordon | A61B 17/7076 | 606/248 |
| 2013/0296940 A1* | 11/2013 | Northcutt | A61B 17/7008 | 606/249 |
| 2014/0081331 A1* | 3/2014 | Zappacosta | A61B 17/7068 | 606/249 |
| 2014/0309741 A1* | 10/2014 | Ganter | A61F 2/4455 | 623/17.16 |
| 2016/0015432 A1* | 1/2016 | Northcutt | A61F 2/44 | 606/249 |
| 2016/0030194 A1* | 2/2016 | Ledet | A61F 2/44 | 623/17.16 |
| 2018/0036132 A1* | 2/2018 | Wu | A61F 2/4455 | |
| 2021/0161677 A1* | 6/2021 | Northcutt | A61B 17/7065 | |
| 2021/0186584 A1* | 6/2021 | Salvermoser | A61B 17/1606 | |

* cited by examiner

SPINAL IMPLANT FOR MOTION PRESERVATION OR FUSION

RELATED APPLICATIONS

This application claims priority from U.S. Provisional Patent Application Ser. No. 62/840,230, filed Apr. 29, 2019, which is incorporated herein by reference in its entirety.

BACKGROUND

This invention relates generally to the field of interspinous and interlaminal fusion surgery and more specifically to interspinous fusion implants and interspinous posterior devices (IPDs), which are used to treat lumbar spinal degenerative disease, such as spinal stenosis, degenerative spondylolisthesis and neurogenic claudication.

Although disc degeneration is one reason for chronic lower back pain, the primary reason for back pain is the instability of the lumbar spine. Instability has been defined as the clinical status of patients with back problems who, with the least provocation, transition from being mildly symptomatic to experiencing a severe episode. Instability results from the inability to maintain control of the lumbar neutral zone, where spine motion occurs with minimal internal resistance and within normal physiological limits. Instability has been generally found to be the source of pain in the lower back.

Lumbar spinal fusion is a common surgical treatment used in disc degeneration, which is related to chronic lower back pain and other spinal disorders, such as disc herniation, spondylolisthesis, facet arthropathy, and spinal stenosis. Over the last 50 years, spinal fusion has become the gold standard for treatment of several degenerative spinal disorders. Despite the many benefits of fusion surgery, there are several complications associated with this technique, including adjacent segment degeneration and psuedoarthrosis. Biomechanical studies have shown that fusion surgeries cause increased motion loading, which increases the stress placed on adjacent vertebral segments. Long-term clinical studies have shown radiographic degenerations of the adjacent vertebral segments. As a result, additional surgeries are often required to treat adjacent segment degeneration after lumbar fusion surgeries.

In an attempt to solve this problem, motion preservation surgeries have been developed over the years along with new non-dynamic and dynamic stabilization devices that avoid total fusion. Motion sparing IPDs have been designed to off-load the posterior facets and annulus and to control motion in defined planes. The idea is that by stabilizing vertebral motion, pain may be minimized, and the controlled motion may also decrease the secondary effects of fusion. Transferring the load from a degenerated disc or fact to a dynamic stabilization construct, while preserving segmental motion, is an important feature required to develop novel dynamic stabilization devices.

The earliest example of a non-dynamic device is the Wallis interspinous implant. The device's original design was a titanium blocker that was inserted between adjacent processes and held in place with a polyester band wrapped around the spinous process above and below the blocker. After this first-generation device showed positive results, a second generation of interspinous implants were developed. The primary change was in the material used for the interspinous spacer. It was changed from titanium to polyetheretherketone (PEEK), a strong, plastic-like polymer that has more elasticity and is therefore less rigid than the previously used material. The implant has notches that fit the physiological shape of the lumbar spine.

Another example is the X-Stop®, which is a titanium interspinous distraction device. This device can be introduced by a minimally invasive approach under local anesthesia and may be useful for treatment of degenerative lumbar spinal stenosis in elderly patients who cannot take general anesthesia because of comorbid conditions. However, some studies have indicated that the X-Stop device has a high rate of failure requiring subsequent surgical reintervention after short-term follow-up in patients with spinal stenosis caused by degenerative spondylolisthesis. Both X-Stop® and the Wallis device are non-dynamic devices and are not capable of dynamic movement.

An example of a dynamic device is the Coflex® Interlaminar Technology device. Coflex® consists of a single, U-shaped component, made from medical grade titanium alloy. The U is positioned horizontally, with is apex oriented anteriorly and the two long arms of the U paralleling the long axis of the spinous processes. The bone facing surfaces are rigid. The wings can be crimped, but they don't have bone securing surfaces or mechanisms. This device allows for both extension and flexion. However, this device is prone to migrate as there is no mechanism to lock the device to the bone. The arms/wings are fixed and can be crimped but cannot be otherwise adjusted to firmly grip the spinous processes. The Coflex® cannot be modified from a dynamic to a non-dynamic device.

A common problem with these dynamic and non-dynamic devices results from loosening failures because there is not enough active fusion mass or bone fixation to resist the physiological loads. Therefore, these stabilization devices are not viable options to treat osteoporotic patients. In addition, the devices are either dynamic or non-dynamic, i.e., there are no devices that provide an all-in-one approach. The result of these deficiencies is a high rate of reoperation, recurrence of symptoms and progression of degenerative changes.

Thus, there is a need for a new IPD that is capable of reliable fixation to bone as well as multi-use as either a dynamic or a non-dynamic system.

SUMMARY

One object of the invention is to provide a better IPD that allows for either a controlled, dynamic movement of vertebrae or fixed non-dynamic implantation all in one device. The present invention allows a surgeon to assess the patient in real-time at the time of the surgical procedure and make decisions about whether or not to use the dynamic feature of the IPD or to implant the device as a non-dynamic IPD.

Another object of the invention is to provide a device in which the size of the opening can be adjusted in real-time during the procedure by the surgeon when applying the non-dynamic implant approach.

Another object of the invention is to allow for the rigid feature of the IPD to be applied by the surgeon as the best option to treat the patient and eliminate stenosis caused back pain and fuse the patient at the same time.

Another object of the invention is that when the implant is no longer beneficial as a dynamic device for the particular patient, a revision of the implant can be done through a small keyhole surgery by inserting a blocker element that will prevent future dynamic movement and transform the dynamic device into a rigid fixation device instantly, which will lead to fusion. This allows for a second surgery to be a minimally invasive, outpatient procedure that can be performed quickly, easily and with the least amount of pain, discomfort, time, and rehabilitation for the patient.

In one embodiment, an interspinous posterior device (IPD) is described. The IPD has a body and bone fixation elements on either side of the body, each of said bone fixation elements having a ratchet locking mechanism for fixing the body to successive spinous processes of a mammalian vertebra. Each of the bone fixation elements is independently adjustable by ratcheting it separately and independently of the other bone fixation elements. The body of the IPD has a dynamic configuration and a non-dynamic configuration, wherein the dynamic configuration allows for both extension and flexion of the successive spinous processes and the non-dynamic configuration prohibits extension of the successive spinous processes. The IPD also includes a removable extension restriction block, wherein the extension restriction block can optionally be inserted in the body to prohibit extension or can be removed from the body to allow extension.

In another embodiment, an IPD includes a U-shaped body that is implantable in between successive spinous processes. The U-shaped body has a longitudinal anterior-posterior axis with a closed rounded anterior end and an open posterior end. The U-shaped body has a superior arm and an inferior arm and a space in between the superior arm and the inferior arm capable of receiving a removable extension restriction block. The U-shaped body is non-dynamic upon receiving the extension restriction block and is dynamic when the extension restriction block is absent from the U-shaped body. The U-shaped body can have a pair of opposing barrels extending in a superior direction from the superior arm, in which each of said barrels has one or more rows of ratchet slots or ratchet teeth. The U-shaped body can have another pair of opposing barrels extending in an inferior direction from the inferior arm, in which each of said barrels has one or more rows of ratchet slots or ratchet teeth. The IPD can also have four cylinders, each cylinder sized to fit within one of the barrels, with each of said cylinders having one or more rows of ratchet teeth that mate with the one or more rows of ratchet slots or ratchet teeth of the barrels. Each cylinder can have spikes on its medial end for engaging with bone of a spinous process, and the rows of ratchet teeth of the cylinders and rows of ratchet slots or teeth of the barrels form a ratchet locking mechanism that locks the cylinders with the barrels thus preventing movement of the barrels in the lateral direction. The IPD can also include a removable extension restriction block that fits within the space between the inferior arm and superior arm of the U-shaped body, such that the extension restriction block mates with the U-shaped body in a lateral movement restricted manner.

In one embodiment, a kit for orthopedic surgical procedures is described. The kit includes an interspinous posterior device (IPD), two or more extension restriction blocks, a tool for implanting the IPD, and a tool for independently manipulating bone fixation elements that are part of the IPD to engage them with the spinous processes or to disengage them from the spinous processes. The IPD has a U-shaped body and bone fixation elements on either side of the body. Each of the bone fixation elements can have a ratchet locking mechanism for fixing the body to successive spinous processes of a mammalian body wherein each of the bone fixation elements is independently adjustable by ratcheting it separately and independently of the other bone fixation elements. The body has a dynamic configuration and a non-dynamic configuration, wherein the dynamic configuration allows for both extension and flexion of the successive spinous processes and the non-dynamic configuration prohibits extension of the successive spinous processes. The extension restriction blocks can optionally be inserted in the U-shaped body to prohibit extension or can be removed from the body to allow extension between successive spinous processes. The two or more extension restriction blocks have different heights. The kit also includes instructions for use that includes the step of inserting the extension restriction block within the U-shaped body if the IPD is to be used as a non-dynamic device allowing only for flexion and not extension of the interspinous processes, and instructions for removing the extension restriction block from the U-shaped body or not inserting it in the first place if the IPD is to be used as a dynamic device allowing for both flexion and extension of the interspinous processes.

In another embodiment, a method of modifying an interspinous orthopedic implant includes the steps of: determining that a patient has a dynamic interspinous posterior device (IPD) implanted between two successive spinous processes; determining that the patient will benefit from modifying the functionality of the IPD from a dynamic device to a non-dynamic device; making a small incision in the back of the patient to access the IPD; inserting an extension restriction block into a body of the IPD thus prohibiting an inferior arm and a superior arm of the IPD from extending toward each other and therefore prohibiting the successive spinous processes from extending toward each other thereby modifying the functionality of the IPD from a dynamic device to a non-dynamic device.

In another embodiment, a method of performing an orthopedic surgical procedure includes the following steps: implanting an interspinous posterior device (IPD) in between two successive interspinous processes of a mammalian subject, wherein the IPD can have the following: a U-shaped body, and bone fixation elements on either side of the body, each of said bone fixation elements having a ratchet locking mechanism for fixing the body to the successive spinous processes, wherein each of the bone fixation elements is independently adjustable by ratcheting it separately and independently of the other bone fixation elements; and the U-shaped body has a dynamic configuration and a non-dynamic configuration, wherein the dynamic configuration allows for both extension and flexion of the successive spinous processes and the non-dynamic configuration prohibits extension of the successive spinous processes. The method further includes the step of determining whether the implant is to be dynamic allowing for extension of the spinous processes or non-dynamic prohibiting extension of the spinous processes. If the implant is to be non-dynamic, inserting an extension restriction block into the U-shaped body to prohibit extension of the spinous processes and independently securing each of the bone fixation elements to the spinous processes.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 7b is an exploded perspective view of the spinous process engagement cylinder assembly of FIG. 7a.

DETAILED DESCRIPTION

Figure 1:
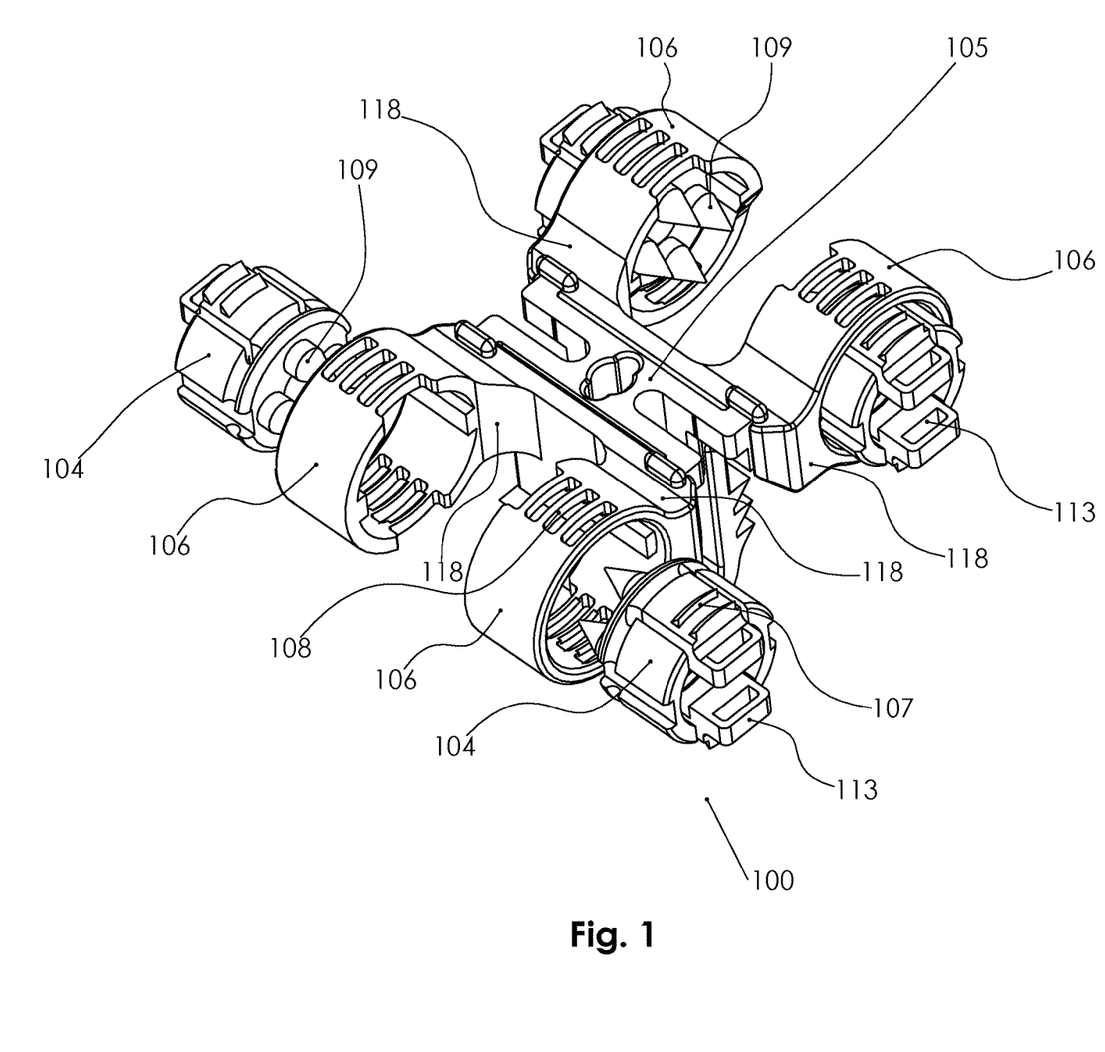
FIG. 1. is a perspective view of one embodiment of a combination dynamic and non-dynamic IPD.
Figure 2:
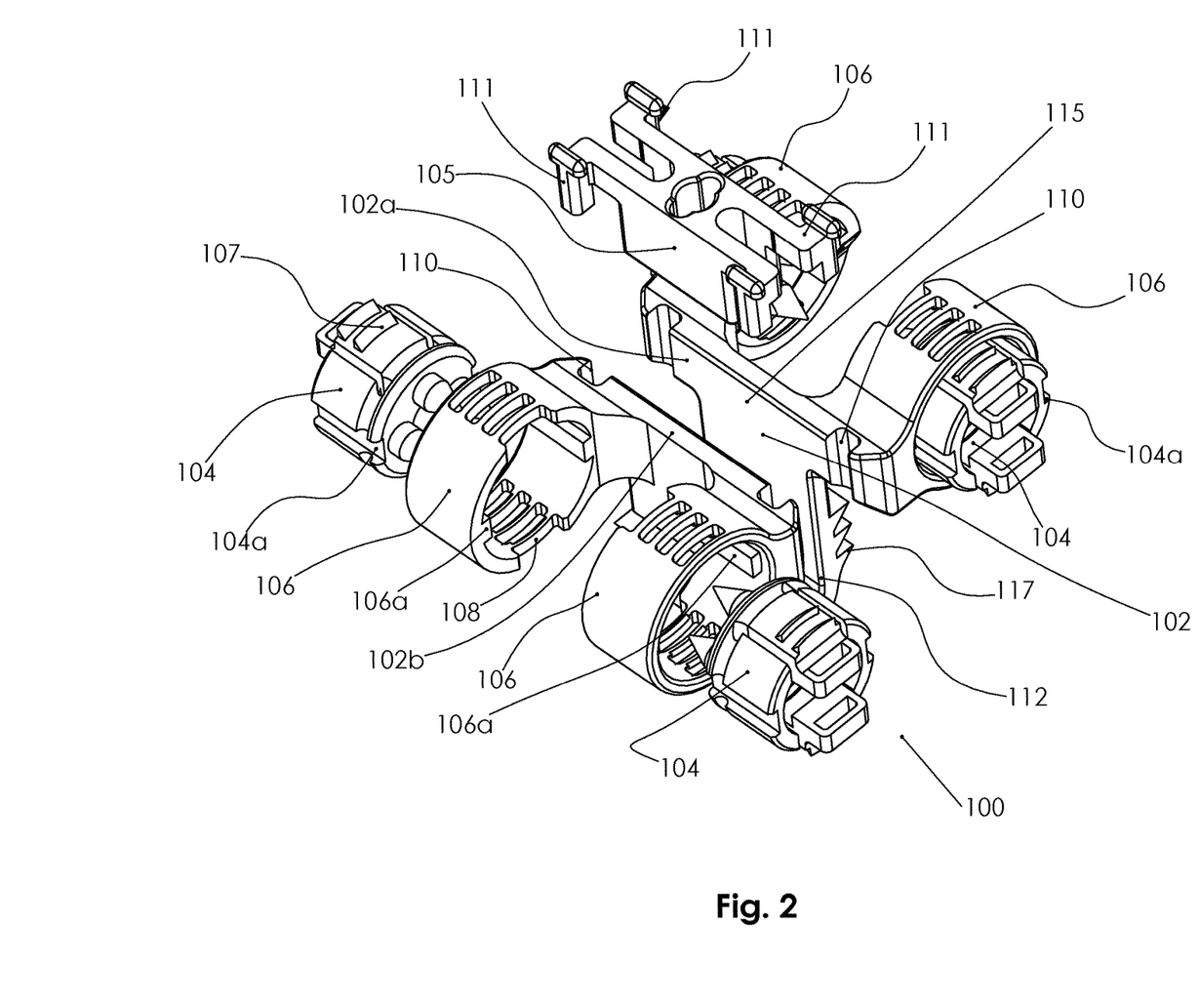
FIG. 2 is an exploded perspective view of the IPD of FIG. 1.

Exemplary embodiments of the invention are shown in the accompanying figures. In accordance with one embodiment, FIGS. 1 and 2 show an IPD 100 made of six components as follows: a U-shaped dynamic implant body 102; four ratchet locking bone engagement cylinders 104; and a removable extension restriction block 105. IPD 100 can be implanted in one of two formations: (i) a rigid, i.e., non-dynamic, formation which utilizes removable block 105; and (ii) a flexible, i.e., dynamic, formation in which removable block 105 is absent.

U-shaped dynamic implant body 102 (hereinafter body 102) has a longitudinal anterior-posterior axis with a closed rounded anterior end 112 and an open posterior end 115 thus forming a U-shape with a superior arm 102a and an inferior arm 102b. The outer surface of anterior end 112 has teeth 117 on the superior arm 102a and inferior arm 102b of the body 102 to secure body 102 to the lamina of the spinous processes. In another embodiment, teeth 117 may be replaced with a rough surface that increases friction with the lamina thus reducing the likelihood that body 102 slips or dislodges after implantation. The inner surface of the U-shaped dynamic implant body 102 can be smooth as shown or have a rough surface as well. Body 102 has an open posterior end 115 that is shaped to receive removable extension restriction block 105. Body 102 has grooves 110 that receive protrusions 111 on block 105. As shown in FIG. 2, body 102 has two superior grooves 110 and two inferior grooves 110 all of which run parallel with each other along the longitudinal anterior posterior axis. Each groove 110 receives a corresponding protrusion 111 on block 105. Block 105 can be inserted into body 102 by lining up protrusions 111 with their corresponding grooves 110 and sliding block 105 through posterior end 115 in an anterior direction toward anterior end 112 of body 102. When block 105 is inserted into body 102, the superior and inferior arms (102a and 102b) of body 102 cannot extend toward each other, because they are blocked or restricted from doing so by block 105. Thus, by inserting block 105 into body 102, IPD 100 is transformed from a dynamic or flexible IPD that allows for both extension and flexion between successive interspinous processes, into one that is rigid and non-dynamic in the sense that it no longer permits extension of the successive interspinous processes toward each other. In addition, it is important to note that superior arms 102a may be distracted away from the inferior arms 102b by pushing arms 102a away from arms 102b thus increasing the gap or space between them. This can be accomplished by inserting different sized extension restriction blocks 105. For example, in one embodiment, the gap between arms 102a and 102b in their resting state may be 10 mm, but the gap may be increased to 12 mm by inserting a extension restriction block 105 that is 12 mm in height. This enables surgeons to modify the amount of space between successive spinous processes according to need and is an important feature of the invention.

Body 102 has four bone engagement barrels 106, two on opposite sides of superior arm 102a that extend in a superior direction from superior arm 102a and two on opposite sides of inferior arm 102b that extend in an inferior direction from inferior arm 102b. Each bone engagement barrel 106 is connected to body 102 by a corresponding post 118. Each bone engagement barrel 106 has a pair of opposing columns of parallel slots 108 that receive corresponding teeth 107 on bone engagement cylinders 104. Teeth 107 and slots 108 form a ratchet locking mechanism when they engage with each other. Bone engagement cylinders 104 each have a lateral end with slots 113 that receive an insertion/removal tool for handling the cylinders 104, and a medial end with spikes 109 that engage the spinous processes and secure IPD 100 to the interspinous processes. Bone engagement cylinders 104 each have a pair of grooves 104a on opposite sides of the cylinders 104 that mate with a pair of sliders 106a on the inner wall of barrels 106. Sliders 106a are on opposite sides of barrels 106. When sliders 106a mate with grooves 104a, cylinders 104 cannot spin within barrels 106 and are thus locked in place radially. This is a further means of securing cylinders 104 to barrels 106 and avoiding any issues relating to slippage or dislodgment of IPD 100 from the spinous processes. The ratchet locking mechanism formed by the engagement of teeth 107 with slots 108 reduces or eliminates the risk that IPD 100 will slip or dislodge after implantation thus further reducing the risk of follow-up surgical intervention.

In practice, once body 102 is implanted in between two successive spinous processes, cylinders 104 are inserted in a lateral to medial direction through barrels 106 until spikes 109 firmly engage with the bones of the spinous processes. Once all four cylinders 104 are inserted in the foregoing fashion, IPD 100 is firmly engaged with the spinous processes in a dynamic manner. If the surgeon decides that the implant should be dynamic, then block 105 is not inserted into the space between superior arm 102a and inferior arm 102b. If the surgeon decides that the implant should be non-dynamic and restrict extension of the spinous processes, then block 105 is inserted into the space between superior arm 102a and inferior arm 102b in a posterior to anterior direction toward from posterior end 115 toward anterior end 112 of body 102. This step is performed by aligning protrusions 111 of block 105 with grooves 110 of body 102 and sliding block 105 in a posterior to anterior direction. It is also important to note that each of the cylinders 104 is independently ratchetable relative to the other cylinders. This allows for flexibility within the anatomy and takes into account the different amounts of bone thickness of successive spinous processes. Because the cylinders 104 with the spikes 109 attached are movable independently from each other, they can be adjusted to accommodate a wide range of differing anatomy of patients. Thus, IPD 100 can be implanted and secured on a thicker and a thinner spinous process or lamina at the same time without removal of bone to make IPD 100 fit better, thus preserving bone. This is enabled by the independent ratcheting mechanisms of each cylinder/barrel combination.

In accordance with another embodiment, FIGS. 3-6 show an IPD 200 made of six components as follows: a U-shaped dynamic implant body 202; four ratchet locking bone engagement cylinders 204 (each of which is made of four additional components as described in more detail below with respect to FIGS. 7a and 7b); and a removable extension restriction block 205. IPD 200 can be implanted in one of two formations: (i) a rigid, i.e., non-dynamic, formation which utilizes removable block 205; and (ii) a flexible, i.e., dynamic, formation in which removable block 205 is absent.

Figure 3:
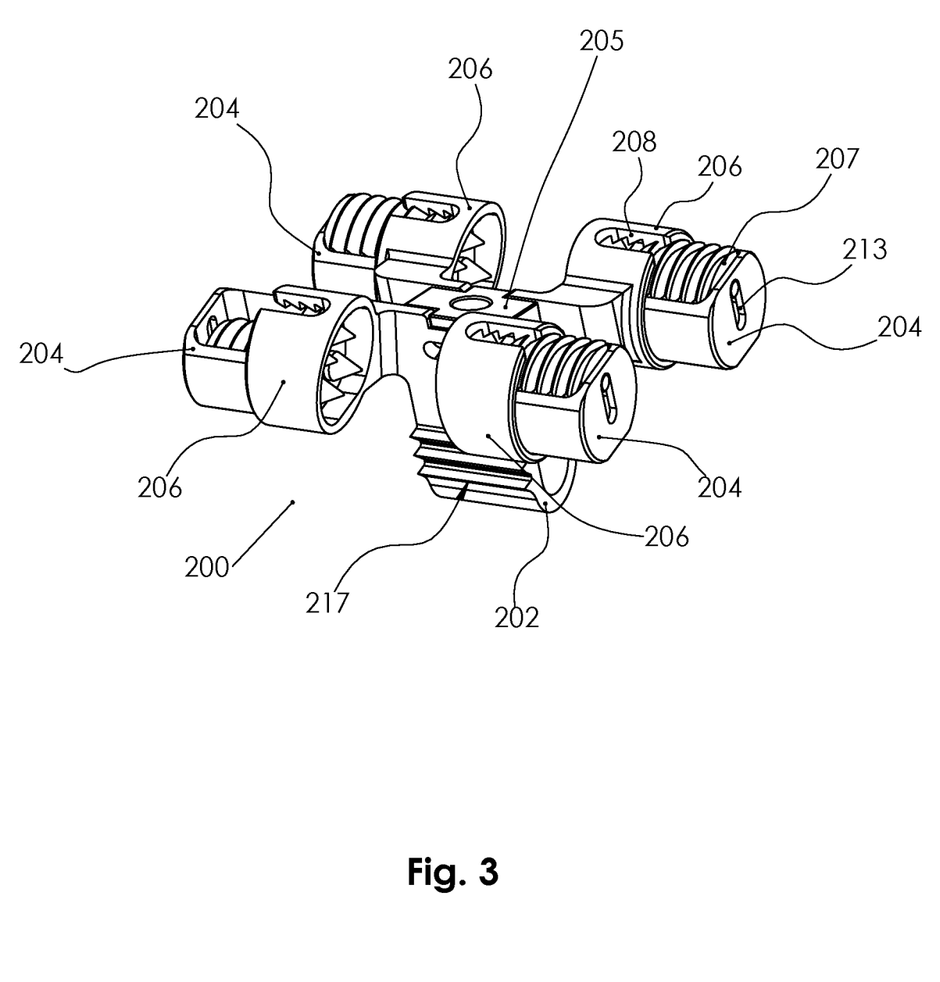
FIG. 3 is a perspective view of a combination dynamic and non-dynamic IPD in accordance with another embodiment.
Figure 4:
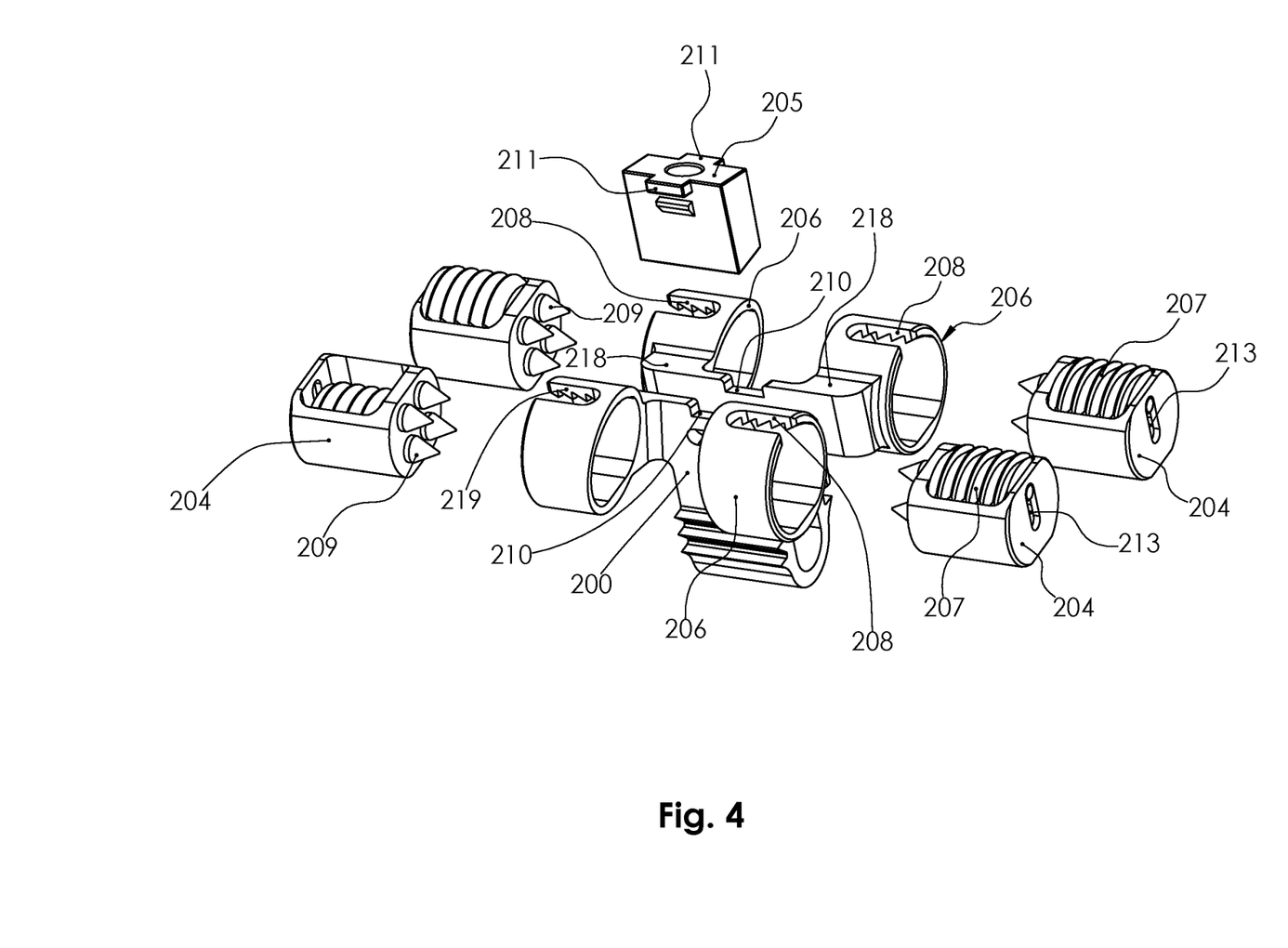
FIG. 4 is an exploded perspective view of the IPD of FIG. 3.

U-shaped dynamic implant body 202 (hereinafter body 202) has a longitudinal anterior-posterior axis with a closed rounded anterior end 212 and an open posterior end 215 thus forming a U-shape with a superior arm 202a and an inferior arm 202b. The outer surface of anterior end 212 has teeth 217 on the superior arm 202a and inferior arm 202b of the body 202 to secure body 202 to the lamina of the spinous processes. In another embodiment, teeth 217 may be replaced with a rough surface that increases friction with the lamina thus reducing the likelihood that body 202 slips or dislodges after implantation. The inner surface of the U-shaped dynamic implant body 202 can be smooth as shown or have a rough surface as well. Body 202 has an open posterior end 215 that is shaped to receive removable extension restriction block 205. Body 202 has notches 210 that receive protrusions 211 on block 205. As shown in FIG. 4, body 202 has one superior notch 210 and one inferior notch 210. Each notch 210 receives a corresponding protrusion 211 on block 205. Block 205 can be inserted into body 202 by lining up protrusions 211 with their corresponding notches 210 and sliding block 205 through posterior end 215 in an anterior direction toward anterior end 212 of body 202. When block 205 is inserted into body 202, the superior and inferior arms (202a and 202b respectively) of body 202 cannot extend toward each other, because they are blocked or restricted from doing so by block 205. Thus, by inserting block 205 into body 202, IPD 200 is transformed from a dynamic or flexible IPD that allows for both extension and flexion between successive interspinous processes, into one that is rigid and non-dynamic in the sense that it no longer permits extension of the successive interspinous processes toward each other. In addition, it is important to note that superior arms 202a may be distracted away from inferior arms 202b by pushing arms 202a away from arms 202b thus increasing the gap or space between them. This can be accomplished by inserting different sized extension restriction blocks 205. For example, in one embodiment, the gap between arms 202a and 202b in their resting state may be 10 mm, but the gap may be increased to 12 mm by inserting an extension restriction block 205 that is 12 mm in height. This enables surgeons to modify the amount of space between successive spinous processes according to need and is an important feature of the invention.

Body 202 has four bone engagement barrels 206, two on opposite sides of superior arm 202a that extend in a superior direction from superior arm 202a and two on opposite sides of inferior arm 202b that extend in an inferior direction from inferior arm 202b. Each bone engagement barrel 206 is connected to body 202 by a corresponding post 218. Each bone engagement barrel 206 has at least one column of ratchet teeth 208 that mate with corresponding ratchet teeth 207 on bone engagement cylinders 204. Teeth 207 and teeth 208 form a ratchet locking mechanism when they engage with each other. Bone engagement cylinders 204 can optionally form a u-shaped channel 219 (as shown) along the length of teeth 208. Bone engagement cylinders 204 each have a lateral end with slots 213 that receive an insertion/removal tool for handling the cylinders 204 and lowering the ratchet teeth 207 to disengage them from teeth 208, and a medial end with spikes 209 that engage the spinous processes and secure IPD 200 to the interspinous processes. The ratchet locking mechanism formed by the engagement of teeth 207 with teeth 208 reduces or eliminates the risk that IPD 200 will slip or dislodge after implantation thus further reducing the risk of follow-up surgical intervention.

In practice, once body 202 is implanted in between two successive spinous processes, cylinders 204 are inserted in a lateral to medial direction through barrels 206 until spikes 209 firmly engage with the bones of the spinous processes. Once all four cylinders 204 are inserted in the foregoing fashion, IPD 200 is firmly engaged with the spinous processes in a dynamic manner. If the surgeon decides that the implant should be dynamic, then block 205 is not inserted into the space between superior arm 202a and inferior arm 202b. If the surgeon decides that the implant should be non-dynamic and restrict extension of the spinous processes, then block 205 is inserted into the space between superior arm 202a and inferior arm 202b in a posterior to anterior direction toward from posterior end 215 toward anterior end 212 of body 202. This step is performed by aligning protrusions 211 of block 205 with notches 210 of body 202 and sliding block 205 in a posterior to anterior direction.

Figure 5:
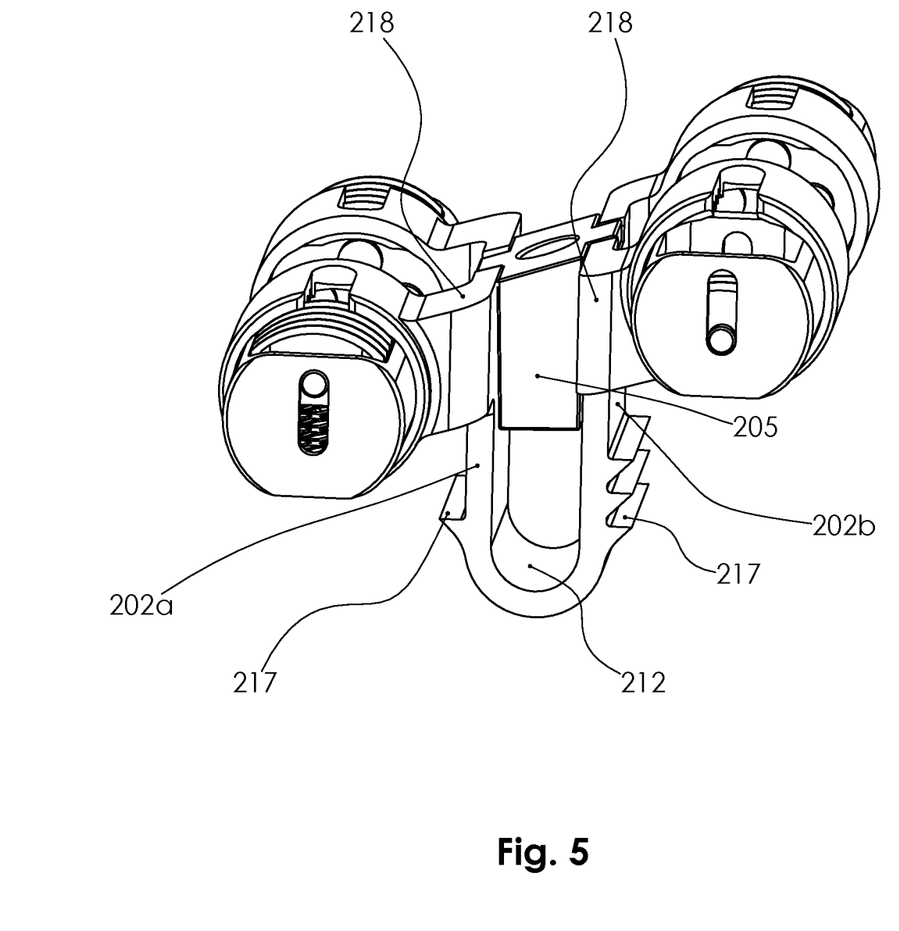
FIG. 5 is a side perspective view of the IPD of FIG. 3.
Figure 6:
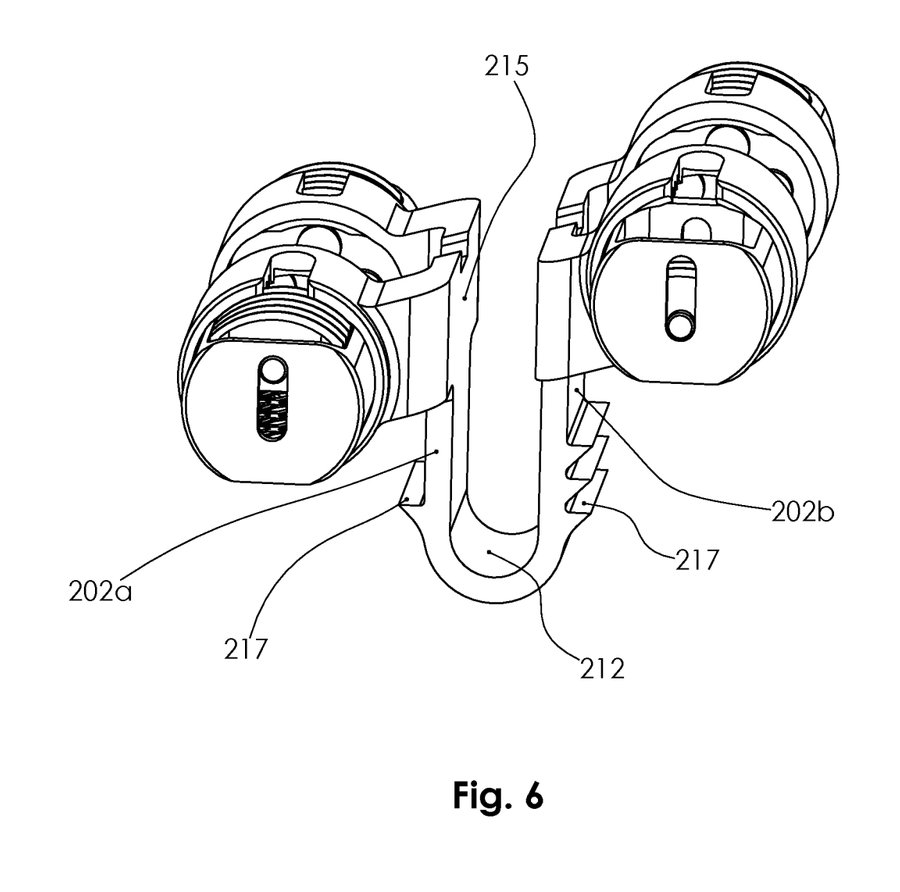
FIG. 6 is another side perspective view of the IPD of FIG. 3.

As shown in FIGS. 5 and 6, superior barrels 206 are offset relative to inferior barrels 206 of IPD 200. This is because superior arm 202a is shorter than inferior arm 202b. In addition, the angle formed between superior arm 202a and superiorly extending barrels 204 is less than ninety degrees so that the barrels are slightly angled towards the anterior direction. In contrast, the angle formed between inferior arm 202b and inferiorly extending barrels 204 is greater than ninety degrees so that the barrels are slightly angled towards the posterior direction. The offset between the superior and inferior barrels allows for a better anatomical fit with spinous processes of the human vertebra.

Figure 7A:
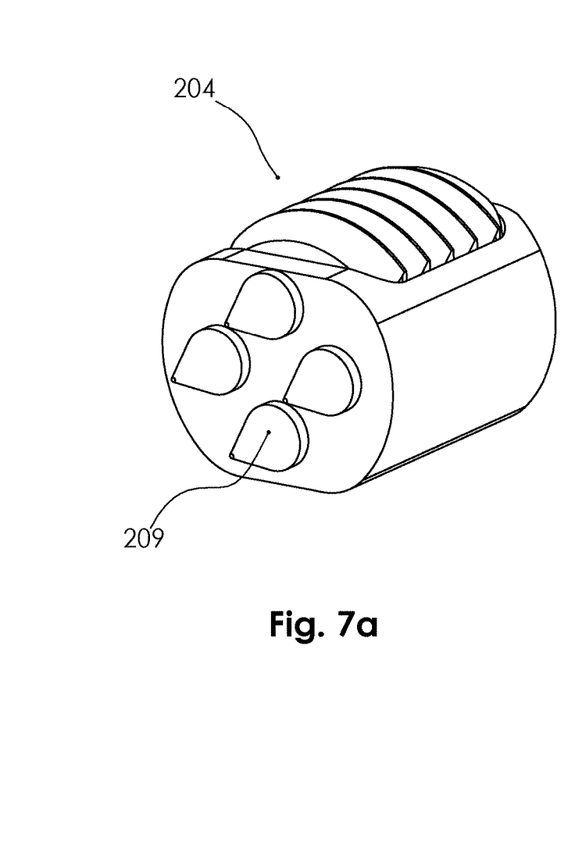
FIG. 7a is a perspective view of a spinous process engagement cylinder assembly.
Figure 7B:
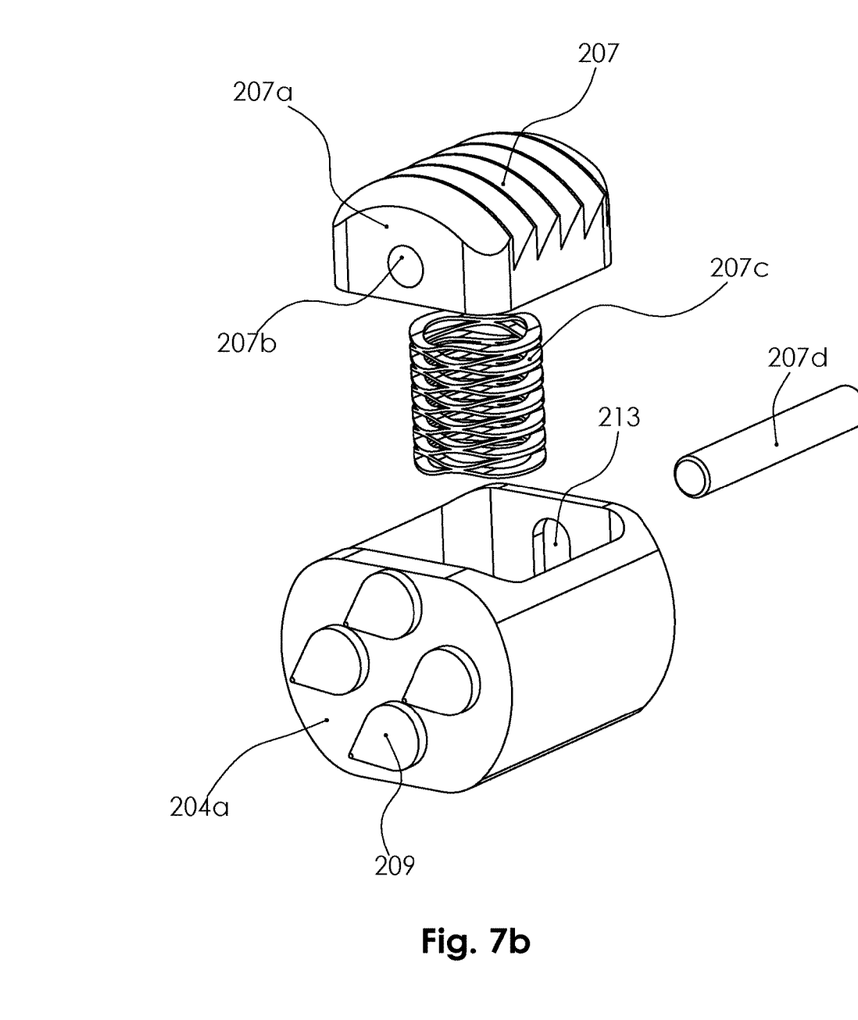

As shown in FIGS. 7a and 7b, the barrels 204 are made of four components that are assembled to form barrels 204 and they are as follows: outer shell 204a; ratchet teeth cap 207; spring 207c; and pin 207d. outer shell 204a has spikes 209 extending from its medial end. On its lateral end is a channel opening 213 that receives pin 207d. Ratchet teeth cap 207 has holes 207b on both its medial and lateral ends (lateral end not shown). Spring 207c sits inside the cavity of outer shell 204a with ratchet teeth cap 207a resting atop it. Pin 207d is inserted through channel opening 213 and through lateral hole 207b extending through ratchet teeth cap 207 and out the medial end through hole 207b on the medial side of ratchet teeth cap 207. The inner medial wall of the cavity of outer shell 204a may have a channel formed therein corresponding and opposite channel opening 213 to receive the medial end of pin 207d. The lateral end of pin 207d rests within channel opening 213 and can travel along a longitudinal axis in the posterior inferior direction. Spring 207c forces ratchet teeth cap 207a toward the posterior direction so that teeth 207 protrude from the open top of outer shell 204a. This configuration forces teeth 207 to engage with teeth 208 of the barrel. Teeth 207 can be disengaged from teeth 208 by using an extraction tool that pushes pin 207d in the anterior direction, thus lowering ratchet teeth cap 207a into the cavity of outer shell 204a and causing teeth 207 to disengage from teeth 208 and allowing he removal of cylinder 204 from barrel 206. This can be done with all four cylinders 204 and their corresponding barrels 206 to allow disengagement of spikes 219 from the spinous process and removal of IPD 200 from the implanted region. It is also important to note that each of the cylinders 204 is independently ratchetable relative to the other cylinders 204. This allows for flexibility within the anatomy and takes into account the different amounts of bone thickness of successive spinous processes. Because the cylinders 204 with the spikes 209 attached are movable independently from each other, they can be adjusted to accommodate a wide range of differing anatomy of patients. Thus, IPD 200 can be implanted and secured on a thicker and a thinner spinous process or lamina at the same time without removal of bone to make IPD 200 fit better, thus preserving bone. This is enabled by the independent ratcheting mechanisms of each cylinder/barrel combination.

In another embodiment, a kit having an IPD is described. The kit can include an IPD body 102 or 202, block 105 or 205 and at least four cylinders 104 or 204. In addition, the kit can contain more than one block in which the multiple blocks are in different sizes in terms of their height in the superior inferior direction. For example, the kit may contain one block that is 14 mm, another bock that is 16 mm and another block that is 12 mm. Block 105 may come in multiple sizes ranging from 10 mm to 20 mm. The kit also includes an insertion tool for inserting and removing cylinders 104 or 204 into barrels 106 or 206 respectively. The kit can also include instructions for use for implanting the IPD, e.g., IPD 100 or IPD 200, and for converting the implanted IPD from a non-dynamic implant to a dynamic implant or from a dynamic implant to a non-dynamic implant.

The IPDs described herein allow modification of the implant with a minor surgical procedure with a small incision. For example, if the implanted IPD is initially in its dynamic formation, a revision of the implant can be done through a small keyhole surgery by inserting the block (e.g., block 105 or 205) in between the superior and inferior arms of the IPD (e.g., 102a and 102b or 202a and 202b respectively) thus transforming the IPD into a non-dynamic rigid device instantly thus allowing and leading to fusion. Thus, a method of treating a patient is described in which a dynamic IPD is transformed into a non-dynamic IPD without removing the IPD from the patient.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims, and that various aspects of the embodiments described herein may be combined with or interchangeable with each other.

We claim:

1. An interspinous posterior device, comprising:
a body; and
bone fixation elements on either side of the body, each of said bone fixation elements comprising a ratchet locking mechanism for fixing the body to successive spinous processes of a mammalian body, wherein each of the bone fixation elements is independently adjustable by ratcheting it separately and independently of the other bone fixation elements;
wherein the body has a dynamic configuration and a non-dynamic configuration, wherein the dynamic configuration is configured to allow for both extension and flexion of successive spinous processes and the non-dynamic configuration configured to prohibit extension of successive spinous processes.

2. The interspinous posterior device of claim 1, further comprising a removable extension restriction block, wherein the extension restriction block can be inserted in the body to prohibit extension or can be removed from the body to allow extension.

3. The interspinous posterior device of claim 2, wherein the body is a U-shaped implantable component having a longitudinal anterior-posterior axis with a closed rounded anterior end and an open posterior end and a superior arm and an inferior arm and a space in between the superior arm and the inferior arm that receives the removable extension restriction block, and wherein the U-shaped implantable component is non-dynamic when combined with the extension restriction block and is dynamic when not combined with the extension restriction block.

4. The interspinous posterior device of claim 3, wherein the body has one or more lateral movement restriction elements and the extension restriction block has one or more lateral movement restriction elements that mates with the one or more lateral movement restriction elements of the body such that when the extension restriction block is inserted into the body, the extension restriction block is prohibited from migrating in a lateral direction within the body.

5. The interspinous posterior device of claim 4, wherein the one or more lateral movement restriction elements of the body comprises one or more grooves and the one or more lateral movement restriction elements of the extension restriction block comprises one or more protrusions that mates with the one or more grooves to prohibit lateral movement of the extension restriction block within the body.

6. The interspinous posterior device of claim 4, wherein the one or more lateral movement restriction elements of the body comprise one or more notches and the one or more lateral movement restriction elements of the extension restriction block comprises one or more protrusions that mates with the one or more notches to prohibit lateral movement of the extension restriction block within the body.

7. The interspinous posterior device of claim of claim 3, wherein when the extension restriction block is inserted into the body, the superior and inferior arms of body cannot extend toward each other, because they are blocked or restricted from doing so by the extension restriction block.

8. An interspinous posterior device comprising:
a U-shaped body that is implantable in between successive spinous processes, said U-shaped body having a longitudinal anterior-posterior axis with a closed rounded anterior end and an open posterior end and a superior arm and an inferior arm and a space in between the superior arm and the inferior arm capable of receiving a removable extension restriction block, and wherein the U-shaped body is non-dynamic upon receiving the extension restriction block and is dynamic when the extension restriction block is absent from the U-shaped body;
a pair of opposing barrels extending in a superior direction from the superior arm, each of said barrels comprising one or more rows of ratchet slots or ratchet teeth;
a pair of opposing barrels extending in an inferior direction from the inferior arm, each of said barrels comprising one or more rows of ratchet slots or ratchet teeth;
four cylinders, each cylinder sized to fit within one of the barrels, each of said cylinders comprising one or more rows of ratchet teeth that mates with the one or more rows of ratchet slots or ratchet teeth of the barrels, wherein each cylinder has spikes on its medial end for engaging with bone of a spinous process and wherein the rows of ratchet teeth of the cylinders and rows of ratchet slots or teeth of the barrels form a ratchet locking mechanism that locks the cylinders with the barrels preventing movement of the cylinders in a lateral direction; and a removable extension restriction block that fits within the space between the inferior arm and superior arm of the U-shaped body, wherein the extension restriction block mates with the U-shaped body in a lateral movement restricted manner.

9. The interspinous posterior device of claim 8, wherein the U-shaped body has one or more lateral movement restriction elements and the extension restriction block has one or more lateral movement restriction elements that mates with the one or more lateral movement restriction elements of the body such that when the extension restriction block is inserted into the body, the extension restriction block is prohibited from migrating in a lateral direction within the U-shaped body.

10. The interspinous posterior device of claim 9, wherein the one or more lateral movement restriction elements of the U-shaped body comprises one or more grooves and the one or more lateral movement restriction elements of the extension restriction block comprises one or more protrusions that mates with the one or more grooves to prohibit lateral movement of the extension restriction block within the U-shaped body.

11. The interspinous posterior device of claim 9, wherein the one or more lateral movement restriction elements of the U-shaped body comprise one or more notches and the one or more lateral movement restriction elements of the extension restriction block comprises one or more protrusions that mates with the one or more notches to prohibit lateral movement of the extension restriction block within the U-shaped body.

12. A kit for orthopedic surgical procedures comprising:
an interspinous posterior device (IPD) comprising:
a U-shaped body; and
bone fixation elements on either side of the body, each of said bone fixation elements comprising a ratchet locking mechanism for fixing the body to successive spinous processes of a mammalian body wherein each of the bone fixation elements is independently adjustable by ratcheting it separately and independently of the other bone fixation elements;
wherein the body has a dynamic configuration and a non-dynamic configuration, wherein the dynamic configuration is configured to allow for both extension and flexion of the successive spinous processes and the non-dynamic configuration is configured to prohibit extension of the successive spinous processes;
two or more removable extension restriction blocks, wherein the extension restriction blocks can be inserted in the U-shaped body to prohibit extension or can be removed from the body to allow extension between successive spinous processes, and wherein the two or more extension restriction blocks have different heights;
a tool for implanting the U-shaped body;
a tool for independently manipulating the bone fixation elements to engage them with the spinous processes or to disengage them from the spinous processes; and
instructions for use comprising the step of removing an extension restriction block from the U-shaped body or not inserting it in the first place if the IPD is to be used as a dynamic device allowing for both flexion and extension of the interspinous processes, and further comprising the step of removing the extension restriction block from the U-shaped body or not inserting it in the first place if the IPD is to be used as a dynamic device allowing for both flexion and extension of the interspinous processes.

13. A method of modifying an interspinous orthopedic implant comprising the steps of:
determining that a patient has a dynamic interspinous posterior device (IPD) implanted between two successive spinous processes;
determining that the patient will benefit from modifying the functionality of the IPD from a dynamic device to a non-dynamic device;
making a small incision in the back of the patient to access the IPD;
inserting an extension restriction block into a body of the IPD thus prohibiting an inferior arm and a superior arm of the IPD from extending toward each other and therefore prohibiting the successive spinous processes from extending toward each other thereby modifying the functionality of the IPD from a dynamic device to a non-dynamic device.

14. A method of performing an orthopedic surgical procedure comprising the steps of:
implanting an interspinous posterior device (IPD) in between two successive interspinous processes of a mammalian subject, wherein the IPD comprises:
a U-shaped body; and
bone fixation elements on either side of the body, each of said bone fixation elements comprising a ratchet locking mechanism for fixing the body to the successive spinous processes, wherein each of the bone fixation elements is independently adjustable by ratcheting it separately and independently of the other bone fixation elements;
wherein the U-shaped body has a dynamic configuration and a non-dynamic configuration, wherein the dynamic configuration allows for both extension and flexion of the successive spinous processes and the non-dynamic configuration prohibits extension of the successive spinous processes;
determining whether the implant is to be dynamic allowing for extension of the spinous processes or non-dynamic prohibiting extension of the spinous processes;
if the implant is to be non-dynamic, inserting an extension restriction block into the U-shaped body to prohibit extension of the spinous processes; and
independently securing each of the bone fixation elements to the spinous processes.

* * * * *